United States Patent
Accisano, III et al.

(10) Patent No.: US 7,909,814 B2
(45) Date of Patent: Mar. 22, 2011

(54) DRAINAGE CATHETER HUB WITH ROTATABLE LEVER HANDLE

(75) Inventors: Nicholas Gerald Accisano, III, Howell, NJ (US); Garlyn W. Hendry, Salt Lake City, UT (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 12/557,348

(22) Filed: Sep. 10, 2009

(65) Prior Publication Data
US 2010/0004636 A1    Jan. 7, 2010

Related U.S. Application Data

(63) Continuation of application No. 11/081,301, filed on Mar. 16, 2005, now abandoned.

(51) Int. Cl.
*A61M 27/00* (2006.01)
*A61M 25/00* (2006.01)

(52) U.S. Cl. .................. 604/541; 604/523

(58) Field of Classification Search .......... 604/326, 604/174, 535, 95.04, 264, 541, 528, 95.01, 604/95.02, 95.03, 95.05, 95, 525, 536, 534, 604/530, 523, 241, 164.04, 130.04, 178, 604/280
See application file for complete search history.

(56) References Cited

U.S. PATENT DOCUMENTS

| | | |
|---|---|---|
| 1,207,479 A | 12/1916 | Bisgaard |
| 3,315,592 A | 4/1967 | Lems |
| 3,513,848 A | 5/1970 | Winston et al. |
| 3,798,687 A | 3/1974 | Stevens |
| 3,924,633 A | 12/1975 | Cook et al. |
| 4,206,910 A | 6/1980 | Biesemeyer |
| 4,573,981 A | 3/1986 | McFarlane |
| 4,586,923 A | 5/1986 | Gould et al. |
| 4,643,720 A | 2/1987 | Lanciano |
| 4,738,667 A | 4/1988 | Galloway |

(Continued)

FOREIGN PATENT DOCUMENTS

WO    WO 2006/098818    9/2006

(Continued)

OTHER PUBLICATIONS

Angiodynamics, Abscession Drainage Catheter: A Quick Guide to the Locking Mechanism, AngioDynamics, Inc., Nov. 1999.
International Search Report and Written Opinion, PCT/US06/03021, mailed Sep. 18, 2007, Accisano et al.
International Search Report and Written Opinion, PCT/US06/03464, mailed Jul. 26, 2007, Accisano et al.
International Search Report and Written Opinion, PCT/US06/03467, mailed Jun. 14, 2006, Accisano et al.
International Search Report and Written Opinion, PCT/US06/29304, mailed Feb. 21, 2007, Accisano et al.

(Continued)

*Primary Examiner* — Kevin C Sirmons
*Assistant Examiner* — William Carpenter
(74) *Attorney, Agent, or Firm* — Stoel Rives LLP

(57) ABSTRACT

A drainage catheter hub having a rotatable lever handle adapted to secure a suture thread to maintain the anchor configuration of the distal end of the catheter to secure the position of the catheter within the patient's body. The rotatable lever handle has a released position for allowing movement of the suture and a secured position for preventing movement of the suture. A suture securement ridge adapted to secure the proximal portion of the suture that may otherwise remain loose during the procedure. The rotatable lever handle and associated rotatable barrel can be depressed relative to hub body in a locked configuration to prevent inadvertent rotational movement of the rotatable lever handle and a release slot or release button that can be actuated by the practitioner to allow for rotational movement of the rotatable lever handle.

11 Claims, 8 Drawing Sheets

U.S. PATENT DOCUMENTS

| | | | |
|---|---|---|---|
| 4,740,195 A | | 4/1988 | Lanciano |
| 4,787,892 A | | 11/1988 | Rosenberg |
| 4,885,503 A | | 12/1989 | Takahashi et al. |
| 5,019,054 A | * | 5/1991 | Clement et al. .............. 604/248 |
| 5,052,998 A | | 10/1991 | Zimmon |
| 5,074,484 A | | 12/1991 | Kray |
| 5,078,684 A | | 1/1992 | Yasuda |
| 5,213,575 A | | 5/1993 | Scotti |
| 5,224,935 A | | 7/1993 | Hollands |
| 5,308,318 A | | 5/1994 | Plassche, Jr. |
| 5,352,198 A | | 10/1994 | Goldenberg et al. |
| 5,399,165 A | * | 3/1995 | Paul, Jr. .................... 604/95.04 |
| 5,419,764 A | | 5/1995 | Roll |
| 5,489,269 A | | 2/1996 | Aldrich et al. |
| 5,506,202 A | | 4/1996 | Vertesy et al. |
| 5,522,400 A | | 6/1996 | Williams |
| 5,549,331 A | | 8/1996 | Yun et al. |
| 5,666,970 A | | 9/1997 | Smith |
| 5,693,083 A | | 12/1997 | Baker et al. |
| 5,704,926 A | | 1/1998 | Sutton |
| 5,730,724 A | | 3/1998 | Plishka et al. |
| 5,730,730 A | | 3/1998 | Darling, Jr. |
| 5,806,202 A | | 9/1998 | Blackman et al. |
| 5,893,880 A | | 4/1999 | Egan et al. |
| 5,904,648 A | | 5/1999 | Arndt et al. |
| 5,941,849 A | | 8/1999 | Amos, Jr. et al. |
| 6,159,177 A | | 12/2000 | Amos et al. |
| 6,165,183 A | | 12/2000 | Kuehn et al. |
| 6,231,542 B1 | | 5/2001 | Amos et al. |
| 6,358,271 B1 | | 3/2002 | Egan et al. |
| 6,454,740 B1 | * | 9/2002 | Mody ........................ 604/95.04 |
| 6,508,789 B1 | | 1/2003 | Sinnott et al. |
| 6,547,761 B2 | | 4/2003 | Liu |
| 6,673,060 B1 | | 1/2004 | Fleming, III |
| 6,699,233 B2 | | 3/2004 | Slanda et al. |
| 7,087,038 B2 | | 8/2006 | Lee |
| 7,217,256 B2 | | 5/2007 | Di Palma |
| 7,338,475 B2 | | 3/2008 | Brown |
| 7,578,814 B2 | | 8/2009 | Accisano et al. |
| 7,641,630 B2 | | 1/2010 | Accisano, III et al. |
| 2004/0059293 A1 | | 3/2004 | Chu et al. |
| 2005/0070821 A1 | | 3/2005 | Deal et al. |
| 2005/0107739 A1 | | 5/2005 | Palma |
| 2005/0203485 A1 | | 9/2005 | Lee |
| 2006/0129111 A1 | | 6/2006 | Mottola |
| 2006/0206096 A1 | | 9/2006 | Accisano et al. |
| 2006/0212009 A1 | | 9/2006 | Accisano et al. |
| 2006/0217667 A1 | | 9/2006 | Accisano et al. |
| 2007/0032779 A1 | | 2/2007 | Accisano et al. |
| 2007/0078385 A1 | | 4/2007 | Accisano et al. |
| 2007/0083189 A1 | | 4/2007 | Lampropoulos |
| 2008/0097394 A1 | | 4/2008 | Lampropoulos |

FOREIGN PATENT DOCUMENTS

| | | |
|---|---|---|
| WO | WO 2006/098819 | 9/2006 |
| WO | WO 2006/101592 | 9/2006 |
| WO | WO 2007/019074 | 2/2007 |

OTHER PUBLICATIONS

Office Action issued May 28, 2008 in co-pending U.S. Appl. No. 11/078,140.
Interview Summary issued Nov. 25, 2008 in co-pending U.S. Appl. No. 11/078,140.
Amendment and Response to Office Action filed Nov. 26, 2008 in co-pending U.S. Appl. No. 11/078,140.
Statement of Substance of Interview filed Dec. 22, 2008 in co-pending U.S. Appl. No. 11/078,140.
Final Office Action issued Mar. 3, 2009 in co-pending U.S. Appl. No. 11/078,140.
Interview Summary issued Jul. 7, 2009 in co-pending U.S. Appl. No. 11/078,140.
Amendment after Final and Request for Continued Examination filed Sep. 3, 2009 in co-pending U.S. Appl. No. 11/078,140.
Notice of Allowance issued Oct. 13, 2009 in co-pending U.S. Appl. No. 11/078,140.
Office Action issued Sep. 4, 2008 in co-pending U.S. Appl. No. 11/198,642.
Amendment and Response filed Dec. 19, 2008 in co-pending U.S. Appl. No. 11/198,642.
Interview Summary issued Dec. 23, 2008 in co-pending U.S. Appl. No. 11/198,642.
Statement of Substance of Interview filed Jan. 23, 2009 in co-pending U.S. Appl. No. 11/198,642.
Notice of Allowance issued Apr. 20, 2009 in co-pending U.S. Appl. No. 11/198,642.
Issue Notification issued Aug. 5, 2009 in co-pending U.S. Appl. No. 11/198,642.
Request for Continued Examination filed Aug. 24, 2009 in co-pending U.S. Appl. No. 11/198,642.
Final Office Action issued Mar. 10, 2009 in co-pending U.S. Appl. No. 11/081,301.
Amendment and Response filed Dec. 29, 2008 in co-pending U.S. Appl. No. 11/081,301.
Office Action issued Jun. 26, 2008 in co-pending U.S. Appl. No. 11/081,301.
Amendment filed Apr. 23, 2008 in co-pending U.S. Appl. No. 11/081,301.
Office Action issued Oct. 23, 2007 in co-pending U.S. Appl. No. 11/081,301.
Office Action issued Oct. 16, 2008 in co-pending U.S. Appl. No. 11/608,518.
Interview Summary issued Mar. 31, 2009 in co-pending U.S. Appl. No. 11/608,518.
Amendment and Response filed Apr. 16, 2009 in co-pending U.S. Appl. No. 11/608,518.
Notice of Allowance issued Jul. 27, 2009 in co-pending U.S. Appl. No. 11/608,518.
Request for Continued Examination filed Sep. 28, 2009 in co-pending U.S. Appl. No. 11/608,518.
Notice of Allowance issued Feb. 5, 2010 in co-pending U.S. Appl. No. 11/608,518.
Notice of Allowance issued Aug. 5, 2009 in co-pending U.S. Appl. No. 11/078,939.
Amendment and Response filed Mar. 10, 2009 in co-pending U.S. Appl. No. 11/078,939.
Notice of Non-Compliant Amendment issued Jan. 12, 2009 in co-pending U.S. Appl. No. 11/078,939.
Statement of Substance of Interview filed Jan. 2, 2009 in co-pending U.S. Appl. No. 11/078,939.
Interview Summary issued Dec. 2, 2008 in co-pending U.S. Appl. No. 11/078,939.
Proposed Amendments filed Nov. 21, 2008 in co-pending U.S. Appl. No. 11/078,939.
Office Action issued May 21, 2008 in co-pending U.S. Appl. No. 11/078,939.
Request for Continued Examination filed Nov. 5, 2009 in co-pending U.S. Appl. No. 11/078,939.
Notice of Allowance issued Jan. 26, 2010 in co-pending U.S. Appl. No. 11/078,939.
Office Action issued May 6, 2009 in co-pending U.S. Appl. No. 11/507,777.
Interview Summary issued Jul. 17, 2009 in co-pending U.S. Appl. No. 11/507,777.
Amendment and Response filed Aug. 6, 2009 in co-pending U.S. Appl. No. 11/507,777.
Final Office Action issued Sep. 9, 2009 in co-pending U.S. Appl. No. 11/507,777.
Notice of abandonment dated Dec. 1, 2009 in U.S. Appl. No. 11/081,301.
Notice of allowance dated Mar. 19, 2010 in U.S. Appl. No. 11/205,609.
Office action dated Jul. 20, 2009 in U.S. Appl. No. 11/205,609.
Notice of Allowance dated Jun. 16, 2010 in U.S. Appl. No. 11/205,609.

* cited by examiner

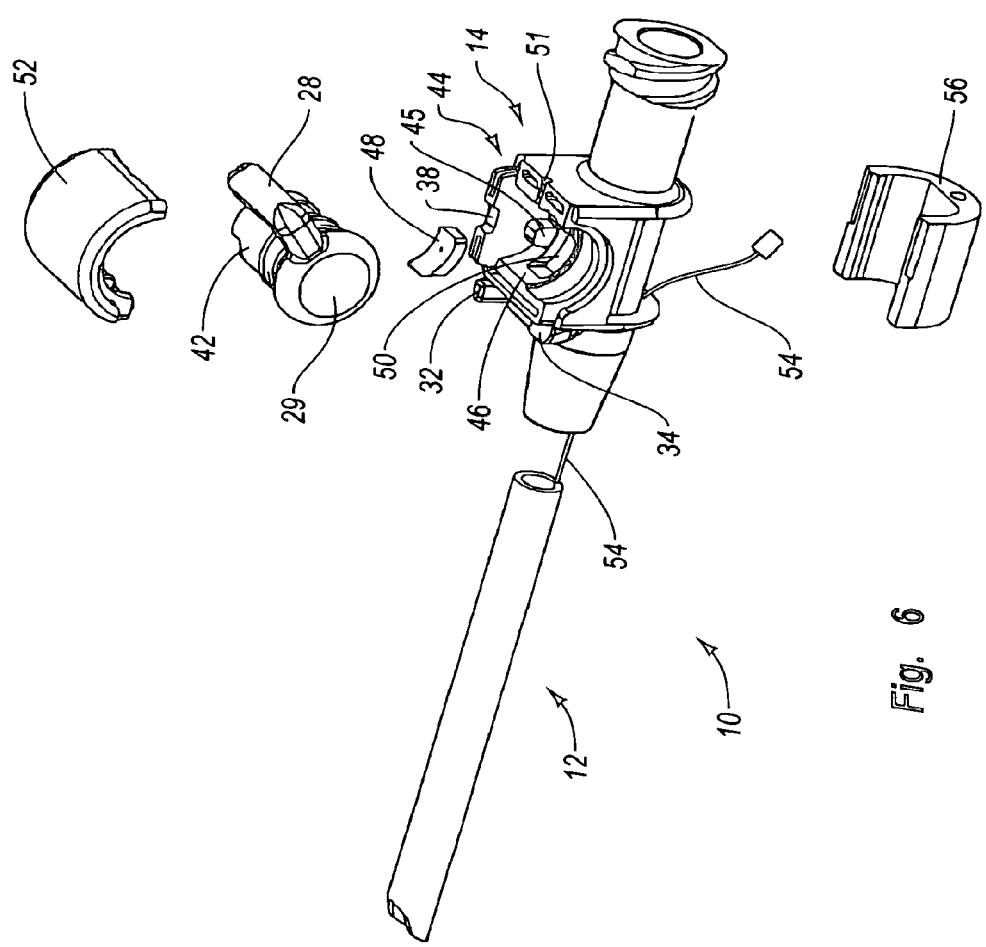

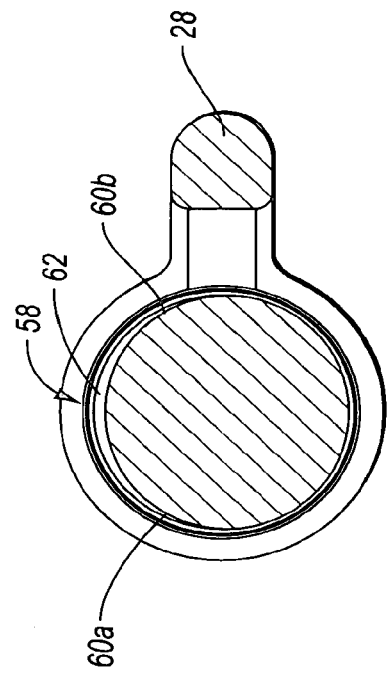
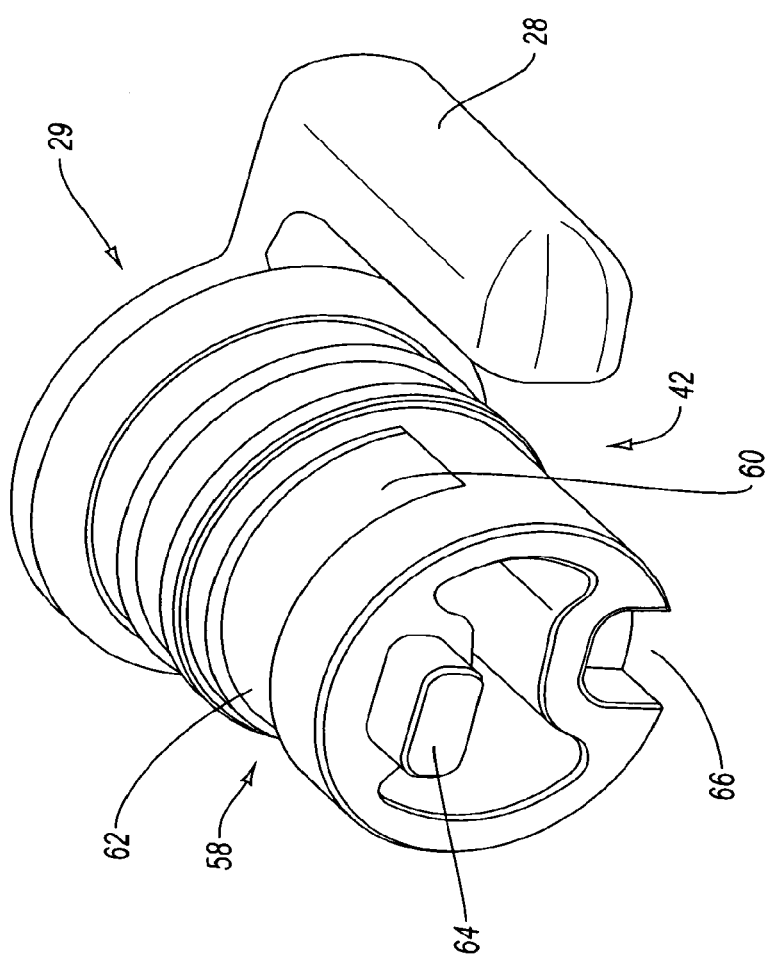
Fig. 7A
Fig. 7B

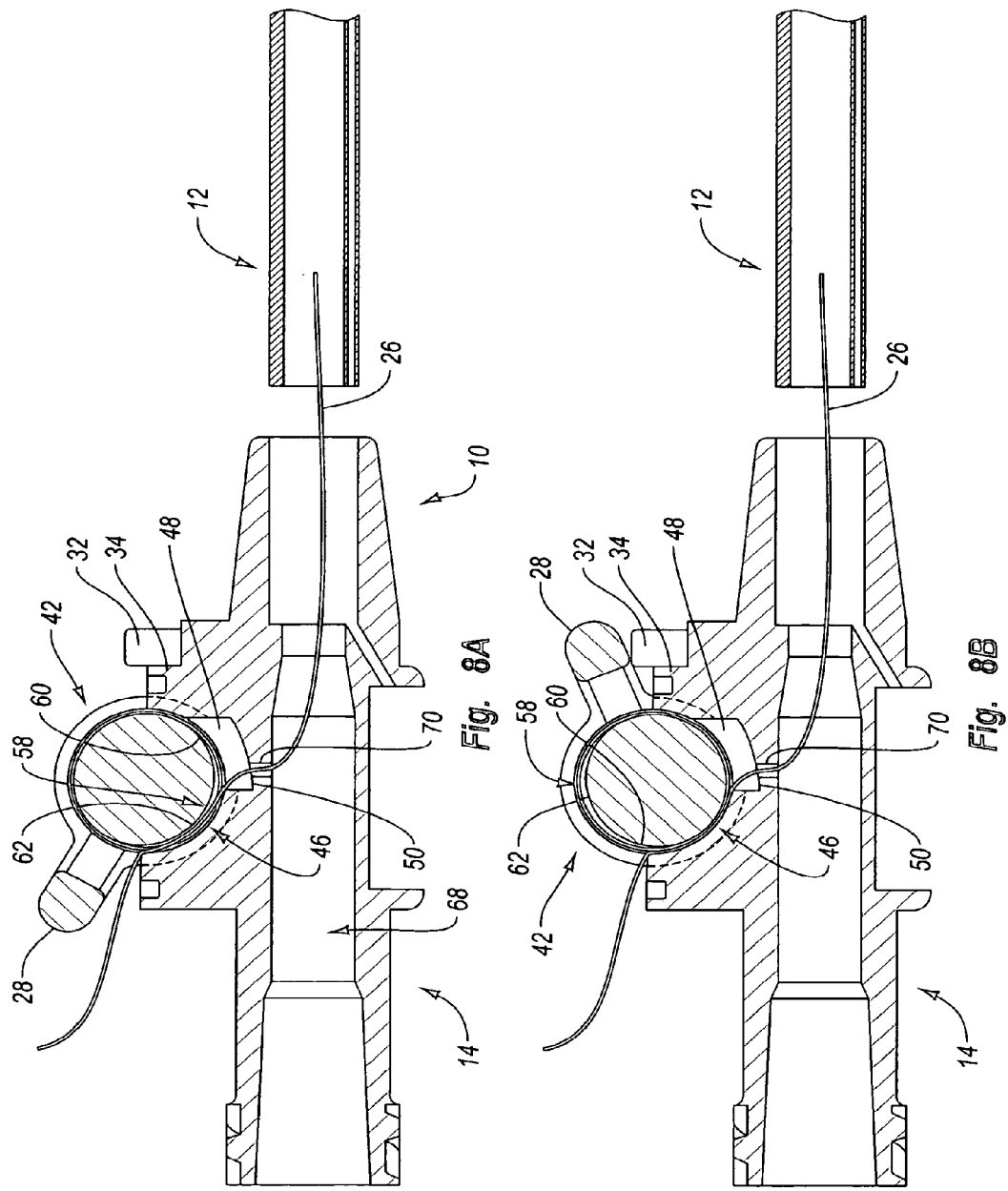

DRAINAGE CATHETER HUB WITH ROTATABLE LEVER HANDLE

CROSS-REFERENCE TO RELATED APPLICATIONS

This patent application is a continuation of U.S. patent application Ser. No. 11/081,301, filed Mar. 16, 2005 now abandoned and entitled DRAINAGE CATHETER HUB WITH ROTATABLE LEVER HANDLE which is incorporated herein by reference.

BACKGROUND OF THE INVENTION

1. The Field of the Invention

The present invention relates to catheters. In more particular, the present invention relates to a drainage catheter hub having a rotatable lever handle adapted to secure a suture thread to maintain the anchor configuration of the distal end of the catheter to secure the position of the catheter within the patient's body.

2. The Relevant Technology

One problem often encountered in modern medicine relates to volumes of fluids that collect in a patient's tissue, body cavities, or other positions within a patient's body that exceed normal volumes. Collected fluids can contribute to infection, exert harmful pressure on the patient's organs, or otherwise impede with proper care and recovery of a patient. Drainage catheters have long been utilized to drain such excess volumes of fluids from a patient's body. Typically, the catheter is adapted to be introduced into the patient to the site where the excess fluid is accumulated. A plurality of drainage bores are positioned in the distal end of the catheter to allow passage of the fluids and any materials suspended in the fluids from the volume of fluid to the drainage bore of the catheter.

The distal end of drainage catheters are typically adapted to form an anchor configuration to secure the drainage catheter at the site where excess fluid is accumulated. However, the tissue surrounding drainage sites often does not provide a solid or reliable substrate to maintain the position of the catheter. As a result, the anchor configuration of the catheter is typically formed in a relatively large pigtail type loop that provides a reliable anchor regardless of the characteristics of the surrounding tissue. The pigtail loop is formed by curling the tip of the catheter tube such that the tip of the catheter contacts a more proximal position on the catheter tube. This is accomplished utilizing a suture that is threaded between the proximal position and the tip of the catheter. When the suture is foreshortened, the tip of the catheter is securely positioned relative to the proximal position on the catheter tube. The portion of the distal end of the catheter tube between the tip of the catheter and the proximal position where the suture exits the catheter tube forms a resulting pig-tail type loop.

The suture is adapted to run the length of the catheter and exit the catheter at the proximal end of the catheter tube. This allows the user to manipulate the suture to maintain or release the anchor configuration of the distal end of the catheter while the distal end of the catheter is positioned inside the patient. Once the anchor configuration of the distal end of the catheter has been established, the practitioner secures the suture to maintain the anchor configuration of the catheter. Otherwise, inadvertent movement of the patient could pull the suture resulting in separation between the tip of the catheter and the proximal position on the catheter tube where the tip of the catheter tube is secured by the suture. Conventionally, a practitioner wraps or ties the free portion of the suture around the proximal portion of the catheter or proximally positioned catheter hub. However, wrapping or tying of the suture can be somewhat inconvenient to perform and make it difficult to release, reposition the anchor, or withdraw the drainage catheter.

A number of devices have been developed to attempt to secure the suture to maintain the anchor configuration of the distal end of the drainage catheter. One device provides a catheter hub adapted such that the suture is threaded between a proximal portion and a distal portion of the hub. To secure the suture, the proximal portion and the distal portion of the hub are pushed toward one another resulting in clamping of the suture between the proximal portion and the distal portion and minimizing movement of the suture. A number of deficiencies are presented by currently available suture securement devices. Many such devices are difficult to manipulate while manually maintaining tension on the suture thread. Additionally, such devices may provide ease in securing the suture, but are not as easily released to allow subsequent manipulation of the suture. Other devices are not intuitive to practitioners utilizing the devices requiring training or leading to improper usage of the device. Some devices do not effectively secure the suture leading to slippage or undesired placement of the distal end of the catheter within the patient.

BRIEF SUMMARY OF THE INVENTION

The present invention relates to catheters. In more particular, the present invention relates to a drainage catheter hub having a rotatable lever handle adapted to secure a suture thread to maintain the anchor configuration of the distal end of the catheter to secure the position of the catheter within the patient's body. The rotatable lever handle has a released position for allowing movement of the suture and a secured position for preventing movement of the suture.

A practitioner positions the rotatable lever handle in the release position for positioning the distal end of the catheter tube in a desired position within a patient's body, such as a volume of bodily fluid to be drained. In the released position, the distal end of the catheter can be configured in a linear or straightened configuration without being restrained by the suture. Once the distal end of the catheter tube is positioned in the desired position within the patient's body, the practitioner grasps the proximal end of the suture and pulls in a rearward direction. This foreshortens the suture, drawing the tip of the catheter tube to a more proximal position on the catheter tube and forming an anchor loop in the distal end of the catheter tube. The anchor loop prevents removal of the distal end of the catheter from the desired positioning while minimizing injury to the patient.

Once the distal end of the catheter is formed into an anchor loop the user rotates the rotatable lever handle to the secured position to maintain the desired positioning of the distal end of the catheter tube within the patient. In the secured position, movement of the suture is prevented and the anchor loop configuration of the distal end of the catheter is maintained. This retains the desired positioning of the distal end of the catheter within the patient and minimizes inadvertent repositioning of the catheter during operation.

According to one embodiment of the present invention, the catheter hub includes a suture securement ridge. The suture securement ridge is adapted to secure the proximal portion of the suture extending from the catheter hub that may otherwise remain loose during the procedure. After the practitioner has rotated the rotatable lever handle to a secured position, the practitioner can then wind the proximal portion of the suture around the suture securement ridge. The practitioner then rotates the rotatable lever handle an additional amount in the secured position such that the rotatable lever handle contacts the suture securement ridge. This prevents unraveling of the proximal portion of the suture wrapped about the suture securement ridge.

Typically, once the drainage catheter is positioned at a desired location within the patient, the drainage catheter remains in the patient for a substantial period of time. According to one embodiment of the present invention, the rotatable lever handle and associated rotatable barrel can be depressed relative to hub body in a locked configuration. The locked configuration prevents inadvertent rotational movement of the rotatable lever handle. As a result, inadvertent movement of the rotatable lever handle by movement of the patient, contact of the handle with clothing, the patient's bed, or other surface is prevented. The catheter hub can also include a release slot or a release button that can be actuated by the practitioner to release the locked configuration of the rotatable lever handle and allow for rotational movement of the rotatable lever handle. This allows the user to rotate the rotatable lever handle to the released position to manipulate the suture or withdraw the catheter.

As will be appreciated by those skilled in the art, a variety of types and configurations of rotatable lever handles and suture securement mechanisms can be utilized without departing from the scope and spirit of the present invention. For example, in one embodiment the rotatable lever handle is positioned to the side of the rotatable barrel rather than around the outer circumference of the catheter hub. In another embodiment, the distal end of the catheter does not form a pigtail-type loop when in the anchor configuration. In another embodiment, the suture is utilized in connection with a release stylet such that the suture can be released by the rotatable lever handle or the stylet.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 6 is an exploded view of the catheter hub of FIG. 1 illustrating the components of the hub.

FIG. 7A is a close up perspective view of the rotatable lever handle and a rotatable barrel utilized in connection with the rotatable lever handle illustrating a cam surface of the rotatable barrel.

FIG. 7B is a close-up end view of the rotatable barrel illustrating the relief of the cam surface relative to the outer circumference of the rotatable barrel.

FIG. 8A is a cross-sectional side view of the catheter hub illustrating the manner in which the rotatable lever handle and the rotatable barrel allow movement of the suture when the rotatable lever handle is in a released position.

FIG. 8B is a cross-sectional side view of the catheter hub illustrating the manner in which the rotatable lever handle and the rotatable barrel secure the suture when the rotatable lever handle is in a secured position.

DETAILED DESCRIPTION OF THE PREFERRED EMBODIMENTS

The present invention relates to catheters. In more particular, the present invention relates to a drainage catheter hub having a rotatable lever handle adapted to secure a suture thread to maintain the anchor configuration of the distal end of the catheter to secure the position of the catheter within the patient's body. The rotatable lever handle has a released position for allowing movement of the suture and a secured position for preventing movement of the suture. According to one embodiment of the present invention, the catheter hub includes a suture securement ridge adapted to secure the proximal portion of the suture that may otherwise remain loose during the procedure. According to one embodiment of the present invention, the rotatable lever handle and associated rotatable barrel can be depressed relative to hub body in a locked configuration to prevent inadvertent rotational movement of the rotatable lever handle. The catheter hub can also include a release slot or release button that can be actuated by the practitioner to release the rotatable barrel to allow for rotational movement of the rotatable lever handle including rotating the rotatable lever handle to release the suture.

Figure 1:
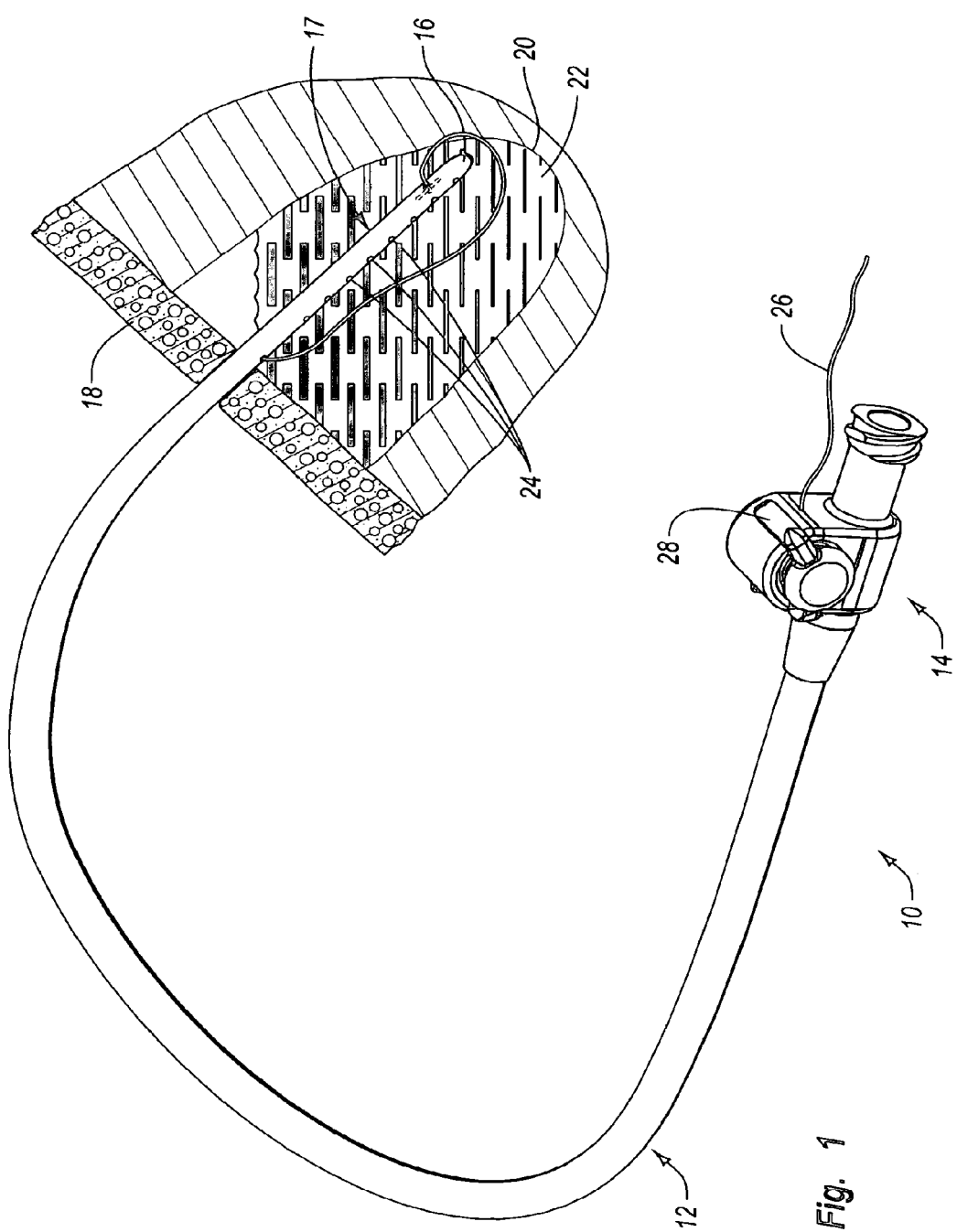
FIG. 1 is a perspective view of a drainage catheter illustrating a catheter hub having a rotatable lever handle in a released position and the catheter tip being introduced into a body cavity of a patient.

FIG. 1 is a perspective view of drainage catheter 10 illustrating a catheter hub 14 having a rotatable lever handle 28 according to one embodiment of the present invention. Drainage catheter 10 is configured to be utilized for potentially prolonged periods to drain fluid from a patient. Catheter hub 14 and rotatable lever handle 28 provide a simple and effective mechanism to allow a user to selectively secure the anchor configuration of a distal end 17 of catheter tube 12 of drainage catheter 10. Rotatable lever handle 28 is adapted to secure a suture thread 26 to maintain the anchor configuration of a distal end of the catheter tube to secure the position of the catheter tube within the patient's body. The rotatable lever handle 28 has a released position for allowing movement of the suture and a secured position for preventing movement of the suture. Rotatable lever handle 28 is shown in the released position in FIG. 1.

In the illustrated embodiment, catheter hub 14 is utilized in connection with catheter tube 12 of drainage catheter 10. Catheter tube 12 comprises an elongate tubular member having a drainage lumen for allowing the passage of fluid from the distal end of catheter tube 12 to catheter tube 12. The configuration of catheter tube 12 allows fluids to be drained from a patient 18 to catheter hub 14. Catheter tube 12 includes a distal end 17. In the illustrated embodiment, distal end 17 is shown being introduced into a body cavity 20 of patient 18. Distal end 17 is positioned in a straightened configuration to facilitate the introduction of distal end 17 into a body cavity 20 of patient 18. Distal end 17 is introduced into body cavity 20 at a position configured to optimize the drainage of the volume of fluid 22 from cavity 20. A plurality of drainage bores 24 are positioned in the distal end 17 of catheter tube 12. The plurality of drainage bores permit the passage of fluids from cavity 20 to the lumen of catheter tube 12. The fluids can then flow along the length of catheter tube 12 and exit catheter hub 14. The fluids can then be passed to a biological disposal container or other disposal reservoir.

In the illustrated embodiment, suture 26 is utilized in connection with catheter tube 12 and catheter hub 14. Suture 26 is adapted to facilitate and maintain formation of an anchor loop configuration in distal end 17 of catheter tube 12. Suture 26 runs from catheter hub 14, along the length of catheter tube, exits a catheter tube 12 at a suture exit bore 27, and is then secured to tip 16 of catheter tube 12. Catheter hub 14 allows securement or release of suture 26. Rotatable lever handle 28 is utilized to allow a user to either secure or release suture 26 during the procedure being performed. In the illustrated embodiment, rotatable lever handle 28 is positioned in a released position. When rotatable lever handle 28 is in a released position, the practitioner can manipulate suture 26. This allows the user to straighten distal end 17 of catheter tube 12 during introduction of distal end 17 into body cavity 20 of patient 18. When rotatable lever handle 28 is in a released position, the practitioner can also retract suture 26 to remove the slack in suture 26 in the portion of suture adjacent distal end 17 of catheter tube 12.

As will be appreciated by those skilled in the art, a variety of types and configurations of drainage catheters can be utilized for draining bodily fluids from a patient without departing from the scope and spirit of the present invention. For example, in one embodiment the fluids to be drained exit from a portion of the drainage catheter other than the catheter hub. In another embodiment, the drainage catheter is adapted to be positioned adjacent an organ or in the vasculature of the patient. In another embodiment, the drainage catheter is introduced utilizing a guidewire or rigid stylet.

Figure 2:
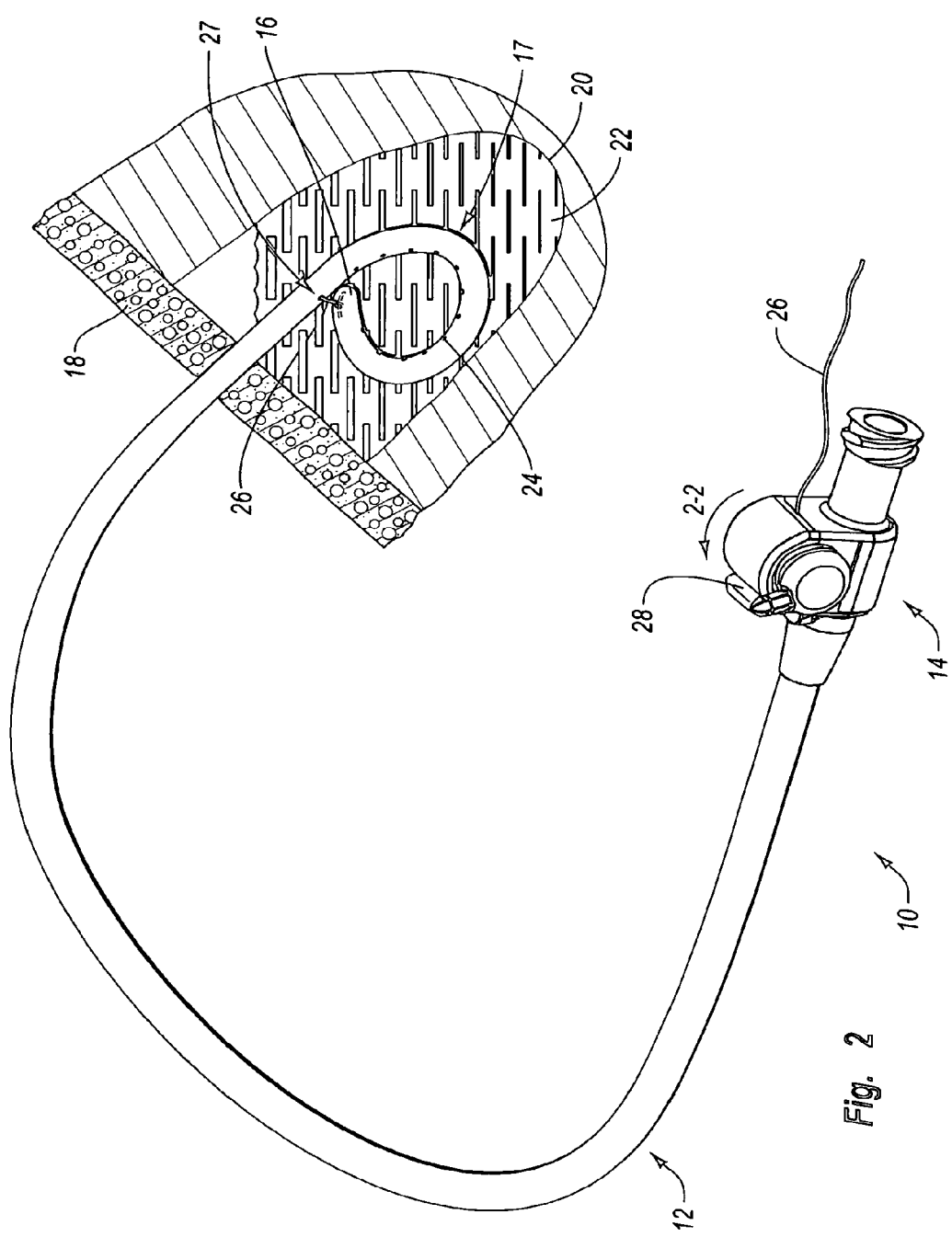
FIG. 2 is a perspective view of the drainage catheter of FIG. 1 illustrating the distal end of the catheter forming an anchor loop and the rotatable lever handle in a secured position.

FIG. 2 is a perspective view of drainage catheter 10 of FIG. 1 illustrating distal end 17 of catheter tube 12 in an anchor loop configuration and rotatable lever handle 28 in a secured position. In the illustrated embodiment, distal end 17 of catheter tube 12 is positioned in a desired location within volume of fluid 22 in body cavity 20. When distal end 17 is positioned in a desired location within the volume of fluid 22, drainage of the volume of fluid 22 can be facilitated in an efficient and advantageous manner.

To maintain the desired positioning of distal end 17 within the body cavity 20 of patient 18, the practitioner grasps the portion of suture 26 extending proximally from catheter hub 14. The user then pulls suture 26 in a rearward direction. Pulling suture 26 in a rearward direction draws tip 16 of catheter tube 12 to a suture exit bore 27. Suture exit bore 27 is a point on catheter tube 12 where suture 26 exits the side wall of catheter tube 12. Suture exit bore 27 is positioned proximally to catheter tip 12. As suture 26 draws tip 16 to suture exit bore 27, distal end 17 forms a pig-tail type anchor configuration. The anchor loop configuration in distal end 17 of catheter tube 12 maintains the position of distal end 17 in body cavity 20 even where the wall of body cavity is insufficiently rigid to secure other catheter securement devices.

Typically, once distal end 17 of catheter tube 12 is positioned in the anchor loop configuration, the drainage catheter 10 will remain positioned within the body of the patient for a considerable period of time to facilitate ongoing drainage of the volume of bodily fluid from the patient. Due to the considerable period of time drainage catheter 10 remains in operation, it is often desirable to maintain the anchor loop configuration of distal end 17 of catheter tube 12 for prolonged periods of time. To maintain the anchor loop configuration of distal end 17 of catheter tube 12, the user rotates rotatable lever handle 28 in the direction of directional arrows 2-2. Rotating rotatable lever handle 28 in the direction of directional arrows 2-2 moves rotatable lever handle 28 from the released position of rotatable lever handle 28 depicted in FIG. 1 to the secured position of rotatable lever handle 28 depicted in FIG. 2. When rotatable lever handle 28 is in the secured position, the components of catheter hub 14 secure suture 26 maintaining the tension on the portion of suture 26 positioned distally to catheter hub 14. As a result, the user can release the portion of suture 26 extending proximally from catheter hub 14 while maintaining the anchor loop configuration of distal end 17 of catheter tube 12.

In the illustrated embodiment, drainage bores 24 are positioned on the inside diameter of distal end 17 when distal end 17 is positioned in the anchor loop configuration. When drainage bores 24 are positioned on the inside diameter of distal end 17, contact by the walls of body cavity 20 on distal end 17 does not obstruct drainage of the volume of volume of fluid 22 from body cavity 20. This can be particularly helpful where the drainage of bodily fluid 22 causes collapse of the walls of body cavity 20 during operation of drainage catheter 10.

Figure 3:
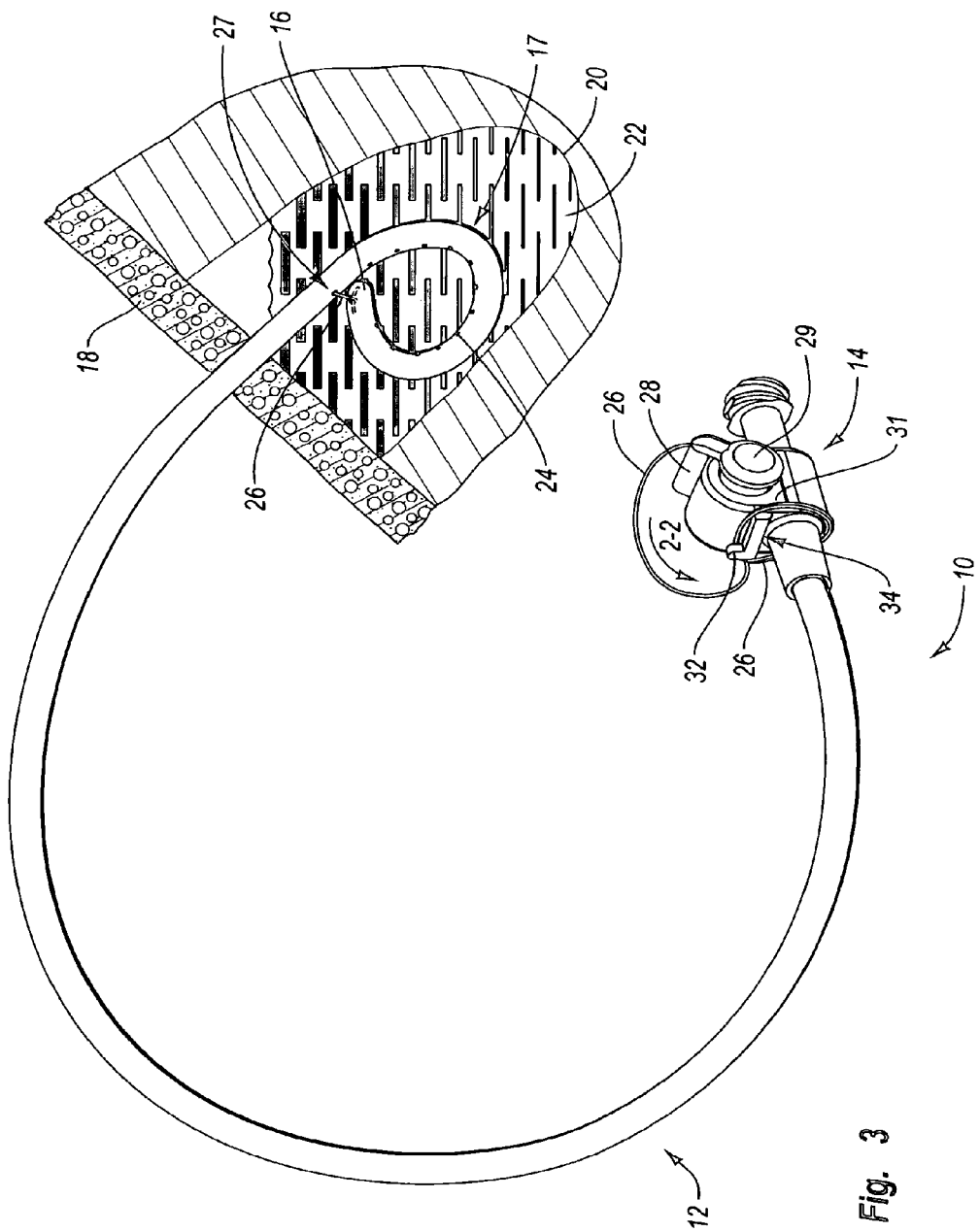
FIG. 3 is a perspective view of the drainage catheter of FIG. 1 illustrating a suture securement ridge of the catheter hub.

FIG. 3 is a perspective view of drainage catheter 10 illustrating the manner in which rotatable lever handle 28 can secure the portion of suture 26 extending proximally from catheter hub 14. In the illustrated embodiment, the orientation of the perspective view has been reversed to more clearly illustrate the components of catheter hub 14 that facilitate securing of the portion of suture 26 extending proximally from catheter hub 14. Once rotatable lever handle 28 has been rotated to the locked position the tension of suture 26 is secured. The practitioner can then release the portion of suture 26 extending proximally from catheter hub 14. However, in some circumstances, the length of the proximal portion of suture 26 can result in tangling of the proximal portion of suture 26 or other undesired interference with suture 26.

In the illustrated embodiment, the proximal portion of suture 26 has been a wrapped around a projection 32 and a suture securement ridge 34. Projection 32 and suture securement ridge 34 are provided on the surface of catheter hub 14 adjacent the connection with catheter tube 12. Projection 32 and securement ridge 34 provide a groove for maintaining the wrapped configuration of a loose portion of suture 26. Projection 32 and securement ridge 34 provide a simple and effective mechanism for securing the loose end of suture 26 when rotatable handle 28 is in a secured position. When the user is ready to remove or reposition anchor loop configuration of distal end 17 of catheter tube 12, the user simply unwraps the suture from projection 32 and suture securement ridge 34. In the illustrated embodiment, a handle base 29 of rotatable handle 28 is shown. Handle base 29 provides a rotation axis about which handle rotates. Additionally, the portion of handle 28 grasped by the practitioner is secured to the internal components of catheter hub 14 utilizing handle base 29. Handle base 29 has an amount of separation from a front surface of rotatable hub 14.

Figure 4:
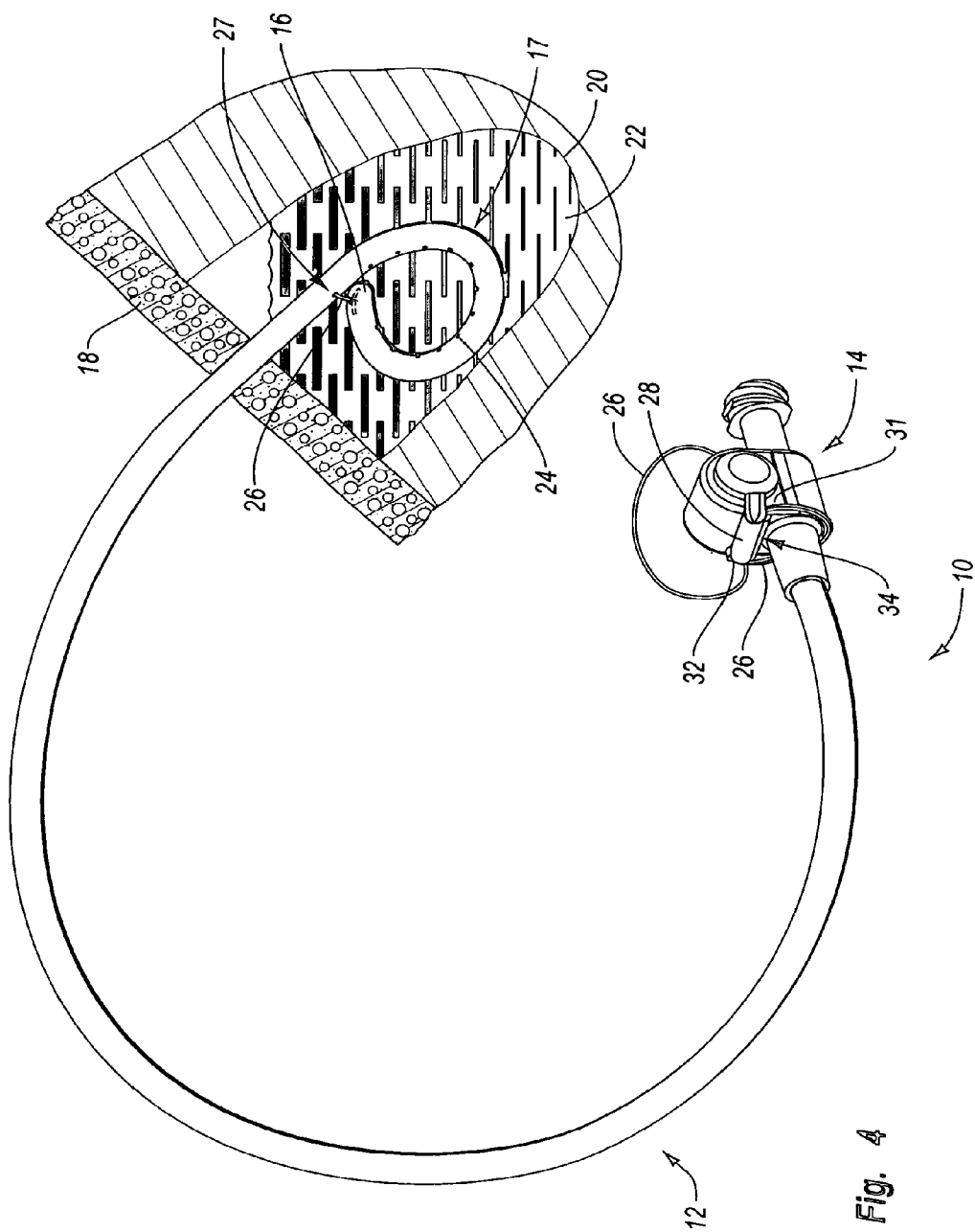
FIG. 4 is a perspective view of the drainage catheter of FIG. 1 illustrating the rotatable lever handle positioned adjacent the suture securement ridge to secure the proximal end of the suture.

FIG. 4 is a perspective view of drainage catheter 10 illustrating rotatable handle 28 in a locked configuration while being positioned adjacent suture securement ridge 34. In the illustrated embodiment, when a user has wrapped the free proximal end of suture 26 about projection 32 and suture securement ridge 34, the user can utilize rotatable handle 28 to maintain the wrapped configuration of suture 26. To utilize rotatable handle 28 to maintain the wrapped configuration of suture 26, the user rotates rotatable handle 28 an additional amount in the direction of suture securement ridge 34. Rotatable handle 28 is configured to contact or be positioned in close proximity with one or both of projection 32 and suture securement ridge 34. In this position, rotatable handle 28 covers the wrapped portion of suture 26 preventing unraveling or slippage of suture 26 from suture securement ridge 34. When rotatable handle 28 is rotated an additional amount to the position depicted in FIG. 4, rotatable handle 28 is in the secured position.

In an alternative embodiment of the present invention, the user can wrap the suture around another portion of the hub such as the catheter tube or the catheter tube engagement member positioned between the catheter tube and the body of the catheter hub. The tail of the suture is threaded between the suture securement ridge and the rotatable handle such that the tail of the suture is locked between the suture securement ridge and the rotatable handle when the rotatable handle is rotated to a locked position. In the embodiment, the rotatable handle is securely positioned adjacent the projection and in contact with the suture securement ridge and pushed into a locked configuration. To release the suture, the user moves the rotatable handle from a locked position, rotates the rotatable handle, and unwraps the suture from the catheter tube or catheter tube engagement member.

In the illustrated embodiment, handle base 29 has been depressed such that it is flush with front surface 31 of catheter hub 14. When handle base 29 is depressed, rotatable handle 28 is locked in the secured position. When rotatable handle 28 is locked in the secured position, rotational forces exerted on rotatable handle 28 will not result in rotation of rotatable handle 28. This prevents inadvertent and undesired rotation of rotatable handle 28 when drainage catheter 10 is in operation. As a result, in the event that the rotatable handle 28 is inadvertently contacted by the patient's clothing, bed, chair or other surface the rotatable handle 28 will not be rotated to the released position. In a typical procedure, the practitioner depresses handle base 29 to a locked position when the anchor loop configuration of distal end 17 of catheter tube is in a desired position, suture 26 has been wrapped about suture securement ridge 34, and portion of suture 26.

As will be appreciated by those skilled in the art, a variety of types and configurations of catheter hubs can be utilized without departing from the scope and spirit of the present invention. For example, in one embodiment only one of a suture securement ridge and a projection are provided with the catheter hub. In another embodiment, one or both the suture securement ridge and projection are provided on the side of catheter hub opposite the catheter tube. In another embodiment, a locking member is provided to secure the suture relative to the securement ridge and the projection that is a separate and distinct component from the rotatable lever handle. In one embodiment, securement ridge and projection provide a groove, slot, taper, channel, or other relief surface to maintain the wrapped position of a free portion of suture. In another embodiment, a secondary mechanism independent of rotatable handle is utilized to lock the secured position of the rotatable handle.

Figure 5:
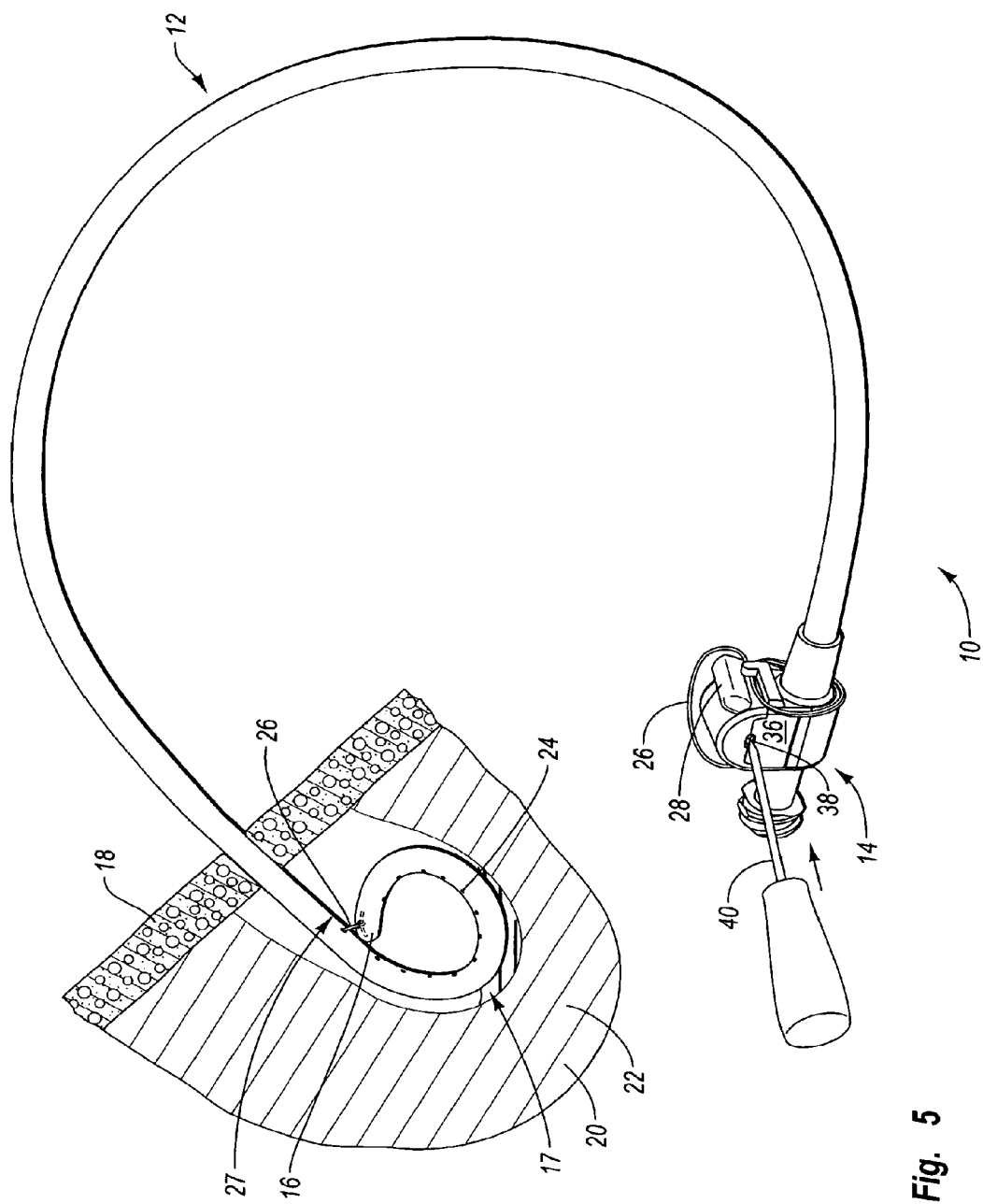
FIG. 5 is a perspective rear view of the drainage catheter of FIG. 1 illustrating a release slot for moving the rotatable lever handle from a locked position to an unlocked position.

FIG. 5 is a rear-perspective view of catheter hub 14 illustrating a release slot 38 for releasing the locked position of rotatable handle 28 allowing rotation of rotatable lever handle 28. In the illustrated embodiment, the volume of fluid 22 in body cavity 20 has been substantially drained. Additionally, the size of body cavity 20 has greatly decreased due to the smaller amount of fluid exerting outward pressure on the walls of body cavity 20. As previously discussed, the anchor loop configuration of the distal end 17 of catheter tube 12 secures the position of distal end 17 in body cavity 20. Additionally, when rotatable handle 28 is in the secured position, the tension on suture 26 is maintained and the tip 16 of catheter tube 12 is secured adjacent suture exit bore 27. When tip 16 of catheter tube 12 is maintained adjacent suture exit bore 27, the anchor loop configuration of distal end 17 of catheter tube 12 is also maintained.

To release the anchor loop configuration of distal end 17 of catheter tube 12, the user must rotate rotatable handle 28 to a released position allowing movement of the length of suture 26. As discussed with reference to FIG. 4, when handle base 29 is depressed to a locked position, the user is prevented from rotating rotatable handle 28. A release slot 38 is provided on the rear surface 36 of catheter hub 14. The user can utilize release slot 38 to move handle base 29 from the locked position to a released position.

Release slot 38 allows a user to insert a pointed tool or other implement to move handle base 29 from a depressed locked position to a non-depressed release position. In the illustrated embodiment, a practitioner is inserting the tip of a hemostat 40 into release slot 38. The tip of hemostat 40 or the tool or implement being utilized by the practitioner contacts a surface interior to release slot 38. The surface interior to release slot 38 conveys forces from the hemostat to handle base 29 to move handle base 29 from the locked position to the released position. The user places a requisite amount of force on hemostat 40 to force handle base to the released position. Once the requisite amount of force has been relayed from the surface interior to release slot 38, handle base 29 is moved to the non-depressed release position and rotatable lever handle 28 can be rotated. The components of catheter hub 14 which operate in connection with handle base 29 and release slot 38 to provide locking and release of rotatable lever handle 28 will be discussed in greater detail with reference to FIGS. 6 and 7A.

As will be appreciated by those skilled in the art, a variety of locking and release mechanisms can be utilized to selectively secure the secured position of the rotatable lever handle. In one embodiment, a button is provided that can be pushed in a first direction to lock the secured position of the rotatable lever handle and pushed in a second direction to allow rotational movement of the rotatable lever handle. In another embodiment, the user locks and unlocks the rotational position of the rotatable lever handle by exerting force directly on the rotatable lever handle. In one exemplary embodiment, the rotatable lever handle can be secured in more than one rotational position.

FIG. 6 is an exploded view of a catheter hub 14 illustrating the component of the catheter hub including the rotatable barrel 42 utilized in connection with rotatable handle 28. In the illustrated embodiment, catheter hub 14 comprises a rotatable lever handle 28, a rotatable barrel 42, a hub body 44, a barrel seat 46, a suture seal 48, a suture seal seat 50, a suture channel 51, a housing 52, a stylet 54, and a stylet release member 56. Rotatable lever handle 28 is integrally coupled to rotatable barrel 42 utilizing handle base 29. Rotatable barrel 42 comprises a substantially cylindrically shaped member positioned perpendicularly to axis of catheter tube 12. Rotatable barrel 42 includes a cam surface (not shown) configured to selectively secure or release suture 26 (see FIG. 5) to secure the tension and/or positioning of suture 26. Rotatable barrel 42 and the cam surface will be discussed in greater detail with reference to FIG. 7A.

Hub body 44 comprises a securement mechanism for holding the internal components of catheter hub 14. Hub body 44 includes a body locking projection 45. Body locking projection 45 comprises a square or rectangular extension of the inner wall of hub body 44. Body locking projection is sized to be positioned in a slot on the mating surface of rotatable barrel 42 when handle base 29 is depressed into a locked position. The mating interaction with body locking projection and the slot in rotatable barrel prevent rotational movement of rotatable barrel 42 and thus rotatable lever handle 28.

Release slot 38 is configured to cooperatively engage a projection of rotatable barrel 42 to prevent rotational movement of rotatable barrel 42. By utilizing release slot 38 and body locking projection 45 with the slot and projection of rotatable barrel 42 provides two points of securement for minimizing rotation of rotatable barrel 42. Release slot 38 allows a user to contact a rear surface or projection of rotatable barrel 42 to move handle base 29 to a non-depressed release position. When the tool or implement utilized by the user to contact the rear surface of rotatable barrel 42, rotatable barrel 42 is slid in the direction away from body locking projection 45. This slides the slot on the rear side of rotatable barrel 42 from cooperative engagement with body locking projection 45 allowing rotational movement of rotatable barrel 42. The rear relief surfaces of rotatable barrel 42 utilized in connection with release slot 38 and body locking projection 45 will be discussed in greater detail with reference to FIG. 7A.

Barrel seat 46 comprises a curved relief surface in hub body 44. Barrel seat 46 is sized to accommodate rotatable barrel 42 to allow for simple and advantageous rotation of rotatable barrel 42 relative to hub body 44. Barrel seat 46 and rotatable barrel 42 are configured to cooperatively engage suture 26 (not shown) to selectively secure suture 26 based on the rotational position of rotatable barrel 42. In one embodiment of the present invention, the barrel and barrel seat are comprised of smooth surface non-compressible materials such as acetyl, Delrine®, polycarbonate, or similar smooth surface materials. Suture seal 48 is configured to be positioned in suture seal seat 50 adjacent rotatable barrel 42. Suture seal 48 provides a fluid tight seal with suture 26 to minimize the leakage of fluids from the main lumen of the catheter hub 14 as suture 26 passes from the main lumen of the catheter hub 14 to the suture seal seat 50. Suture channel 51 provides a passageway for suture 26 (not shown) from the interior of catheter hub 14 to the exterior of catheter hub 14.

A stylet 54 and stylet release member 56 are provided in connection with drainage catheter 10. Stylet 54 and stylet release member 56 are shown separated from one another for the sake of clarity. As will be appreciated by those skilled in the art, sytlet 54 and stylet release member 56 are typically integrally coupled such that movement of stylet release member 56 results in movement of stylet 54. Stylet 54 runs from catheter hub 14 to distal end 17 of catheter tube 12. Stylet 54 provides a securement apparatus for suture 26. A variety of types and configurations of mechanisms can be utilized for providing a stylet and suture combination with a drainage catheter. In the illustrated embodiment, stylet 54 is positioned in a secondary lumen positioned in the sidewall of catheter tube 12. By utilizing a secondary lumen, materials that are drained through the primary lumen of catheter tube 12 do not interfere with proper operation of stylet 54. Stylet 54 and the secondary lumen run from catheter hub 14 to the tip 16 of the catheter tube 12. A small bore at the tip 16 of catheter tube 12 exposes stylet 54 and allows suture 26 to be wrapped around stylet 54.

When the practitioner is ready to remove drainage catheter 10 from the patient, the practitioner disengages stylet release member 56 from its coupling with catheter hub 12. As the user pulls stylet release member 56 in the rearward direction, stylet 54 begins to be withdrawn from the secondary lumen of catheter tube 12. Once stylet 54 is sufficiently withdrawn, stylet 54 is also withdrawn from the position in which it is engaged by suture 26. Since suture 26 is solely secured to the tip of catheter tube 12 utilizing stylet 54, removal of stylet 54 results in release of suture 26. When suture 26 is released, there is nothing to maintain the anchor configuration of distal end of the catheter tube. As a result, as the user begins to withdraw distal end of the catheter tube from the patient's body cavity, distal end of the catheter tube can straighten and easily exit the entry channel of catheter tube 12.

As will be appreciated by those skilled in the art, a variety of types and configurations of catheter hubs can be utilized without departing from the scope and spirit of the present invention. For example, in one embodiment the hub body includes two slots which cooperatively engage two projections of the rotatable barrel. In another embodiment, the rotatable barrel can be locked in a plurality of rotational positions. In another embodiment, the catheter hub does not include a stylet and stylet release member.

FIG. 7A and FIG. 7B illustrate rotatable barrel 42 and rotatable lever handle 28 and a cam surface 58 associated therewith. Cam surface 58 is utilized with rotatable barrel 42 and rotatable lever handle 28 to release and secure suture 26 (not shown). In the illustrated embodiment, rotatable lever handle 28 is secured to rotatable barrel 42 utilizing handle base 29. Rotatable lever handle 28 can be grasped by a user and rotated to change the rotational position of rotatable barrel 42. Rotatable barrel 42 is one example of a cam means.

As will be appreciated by those skilled in the art, a variety of types and configurations of mechanisms for causing rotation of the rotatable barrel can be utilized without departing from the scope and spirit of the present invention. For example, in one embodiment a graspable projection that can be grasped by a user to rotate the rotatable barrel is provided on the face of handle base. In another embodiment, a tool is provided that cooperatively engages the rotatable barrel in a male/female relationship to allow a user to rotate the rotatable barrel.

Cam surface 58 includes a securement portion 60 and a release portion 62. Cam surface 58 extends inwardly from the outside diameter of the rotatable barrel 42 such that the release portion 62 of the cam surface 58 has a greater displacement from the inner contact surface of barrel seat 46 (see FIG. 6) than the securement portion 60. When the rotatable barrel 42 is rotated such that the suture is located between the release portion 62 and the barrel seat (not shown) the suture can be moved by the user. When the rotatable barrel 42 is rotated such that the suture is located between the securement portion 60 and the inner contact surface, the suture is cooperatively engaged between the barrel seat and securement portion 60 to prevent movement of the suture. In the embodiment illustrated in FIG. 7B securement portions 60a and 60b are positioned on both sides of release portion 62. Cam surface 58 is one example of a cam means.

In the illustrated embodiment, rotatable barrel 42 includes a barrel locking projection 64 and a barrel locking slot 66. Barrel locking projection 64 comprises a approximately rectangular shaped projection that extends from the rear surface of rotatable barrel 42. Barrel locking projection 64 is sized to be inserted into release slot 38 (see FIG. 6) of hub body 44 (see FIG. 6) when handle base 29 is depressed into a locking position. When handle base 29 is depressed into a locking position, barrel locking projection 64 slides into the release slot of hub body effectively locking the rotational position of rotatable barrel 42. In the illustrated embodiment, locking projection 64 and release slot 38 (see FIG. 6) of hub body 44 (see FIG. 6) secure the rotational position of rotatable barrel 42 such that the suture is secured by securement portion 60 of cam surface 58. When a user desires to unlock the rotational position of rotatable barrel 42, the user inserts a tool or implement into release slot 38 (see FIG. 6) and pushes locking projection 64 out of engagement with release slot 38. This allows the user to rotate rotatable barrel 42 utilizing rotatable lever handle 28.

Barrel locking slot 66 comprises an approximately square shaped slot which extends inward from the rear surface of rotatable barrel 42. Barrel locking slot 66 is sized to receive body locking projection 45 (see FIG. 6) of hub body 44 (see FIG. 6). When handle base 29 is depressed into a locking position, barrel locking slot 66 slides over the body locking projection of the hub body effectively locking the rotational position of the rotatable barrel 42. Barrel locking slot 66 and the body locking projection provide a secondary point of securement in addition to barrel locking projection 64 and the release slot to secure the rotational position of rotatable barrel 42. When the rotational position of rotatable barrel 42 is secured, the user is prevented from rotating rotatable lever handle 28. When a user pushes locking projection 64 out of engagement with release slot 38 utilizing a tool or other implement, the pushing force is relayed to the other components of rotatable barrel 42 sliding barrel locking slot 66 out of engagement with the body locking projection. The disengagement of barrel locking projection 64 and release slot 38 (see FIG. 6) combined with the disengagement of barrel locking slot 66 and body locking projection allow rotational movement of rotatable barrel 42. This allows the user to rotate rotatable lever handle 28 to the released position allowing movement of the suture and anchor configuration of the distal end of the catheter tube.

As will be appreciated by those skilled in the art, a variety of types and configurations of locking mechanisms can be utilized without departing from the scope and spirit of the present invention. For example, in one embodiment a spring loaded rotatable barrel that maintains a locked position configured to prevent rotation of the barrel is provided. The user depresses the rotatable barrel to disengage the locked position and rotate the barrel. When the user releases the rotatable barrel subsequent to rotation, the spring loaded configuration of the barrel again locks the barrel securing the rotational position of the barrel. In another embodiment, a locking mechanism is provided having components that are separate from the rotatable barrel and the hub body. In another embodiment, the locking mechanism secures the rotational position of the rotatable barrel without depressing the handle base relative to the hub body. In another embodiment, the locking mechanism can secure a plurality of rotatable positions of the locking mechanism.

As will be appreciated by those skilled in the art, a variety of types and configurations rotatable barrels and cam surfaces can be utilized without departing from the scope and spirit of the present invention. For example, in one embodiment, the entire circumference of the rotatable barrel comprises the cam surface and the cam surface is covered with alternating securement portions and release portions such that the rotatable barrel can be rotated continuously while providing alternating locking and releasing of the suture. In another embodiment, the suture is secured using a surface other than the cam surface. In yet another embodiment, a movable member other than the rotatable lever handle is provided to allow the user to selectively secure the suture.

FIGS. 8A and 8B are cross-sectional views of catheter hub 14 and catheter tube 12 depicting the manner in which rotatable barrel 42 secures suture 26. In the illustrated embodiments, catheter tube 12 is coupled to catheter hub 14 utilizing a catheter tube 12 at the distal end of catheter hub 14. The coupling of catheter hub 14 to catheter tube 12 positions a lumen of catheter tube 12 in fluid communication with a main lumen 68 of catheter hub 14. This allows bodily fluids to be drained from the patient, to the lumen of catheter tube 12, and then to main lumen 68 of catheter hub 14 before exiting drainage catheter 10.

Suture 26 is threaded along the length of the lumen of catheter tube 12 and into main lumen 68. As suture 26 passes through the lumen of catheter tube 12, suture 26 extends through main lumen 68. Suture 26 exits main lumen 68 through suture seal seat 50. From suture seal seat 50, suture 26 is threaded along the surface of barrel seat 46 before exiting through suture channel 51 (not shown).

FIG. 8A illustrates rotatable barrel 42 and rotatable lever handle 28 in a released portion. When rotatable barrel 42 is in the released position, release portion 62 of cam portion 58 is positioned adjacent the portion of suture 26 in contact with barrel seat 46. As previously discussed, cam surface 58 extends inwardly from the outside diameter of the rotatable barrel 42 such that the release portion 62 of the cam surface 58 has a greater displacement from the inner contact surface of barrel seat 46 than the securement portion 60. Due to the fact that rotatable barrel 42 is rotated such that suture 26 is located between the release portion 62 and the barrel seat 46 the suture 26 can be moved by the user.

FIG. 8B illustrates rotatable barrel 42 and rotatable lever handle 28 in a secured position. When the rotatable barrel 42 in the secured position the securement portion 60 of cam surface 58 is positioned adjacent the portion of suture 26 in contact with barrel seat 46. In this position, the suture is cooperatively engaged between barrel seat 46 and securement portion 60 effectively preventing movement of suture 26. The pathway of suture 26 provides both an effective conduit for suture 26 to the tip of catheter tube 12 while providing simple and effective manipulation of suture 26. Additionally, the juxtaposition of suture 26 and the components of catheter hub 14 allow a user to simply and efficiently secure the position of suture 26. By being able to secure and release the position of suture 26 the user can secure or release the anchor configuration of the distal end of the catheter tube 12 to position or remove the catheter tube 12 from the patient.

As will be appreciated by those skilled in the art, a variety of types and configurations of sutures can be utilized without departing from the scope and spirit of the present invention. For example, in one embodiment the stylet does not extend to the tip of the catheter tube. In this embodiment, the suture extends to the tip of the catheter tube, exits the catheter tube, and is threaded back to the position on the catheter tube where the stylet terminates to form the anchor configuration of the distal end of the catheter tube. In another embodiment, the suture is threaded from the tip of the catheter tube to the catheter hub in a side lumen positioned in the wall of the catheter tube. In another embodiment, the suture wraps around a majority of the circumference of the rotatable barrel before exiting the catheter hub.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A drainage catheter hub for use with a drainage catheter tube which provides a fluid pathway for draining bodily fluid from a cavity or tissue of a patient, the drainage catheter being configured such that a suture utilized in connection with the drainage catheter selectively secures the proximal end of the catheter in an anchor configuration, the catheter hub configured to be coupled to the distal end of the catheter tube, the drainage catheter hub comprising:
- a hub body comprising a seat having a substantially circular inner contact surface and adapted to be in contact with a portion of the suture while permitting a loose portion of the suture to extend therefrom such that it can be grasped by a user;
- a rotatable barrel, having an axis of rotation and having an outside diameter forming a substantially circular contact surface configured to conform to the substantially circular inner contact surface of the hub body, the rotatable barrel further comprising a cam surface having a release portion and a securement portion, wherein the release portion extends inwardly from the outside diameter of the rotatable barrel a sufficient amount to permit movement of the suture when the suture is positioned between the release portion and the seat and wherein the securement portion is positioned adjacent the seat for cooperatively clamping the suture when the suture is positioned between the securement portion and the seat;
- a rotatable lever handle integrally coupled to the rotatable barrel to rotate the rotatable barrel between a position in which the securement portion contacts the suture to prevent movement of the suture and a position in which the release portion is positioned adjacent the suture to allow movement of the suture;
- a locking mechanism provided in connection with the rotatable lever handle, the locking mechanism configured to secure the rotational position of the rotatable lever handle, wherein the locking mechanism comprises one or more slots on one of the rotatable barrel and the hub body and one or more projections on the other of the rotatable barrel and the hub body, the one or more slots cooperatively engaging the one or more projections when the locking mechanism is actuated; and
- a release mechanism comprising a release slot allowing the user to disengage the one or more projections and the one or more slots for allowing movement of the rotatable lever handle subsequent to actuation of the locking mechanism, wherein the user urges the rotatable lever handle in a direction parallel to the axis of rotation of the rotatable barrel to actuate the locking mechanism.

2. The catheter hub of claim 1, wherein the locking mechanism is integrally coupled to the rotatable barrel and the hub body.

3. The catheter hub of claim 2, wherein the locking mechanism secures the rotatable lever handle in a secured position to prevent movement of the suture.

4. The catheter hub of claim 1, wherein the locking mechanism is a separate and distinct component from the rotatable barrel and the hub body.

5. A drainage catheter hub for use with a catheter tube adapted to be positioned in a body cavity or other position within a patient and utilizing a suture to maintain an anchor configuration in the distal end of the catheter tube, the drainage catheter hub comprising:
- a hub body;
- a cam means for selectively securing a suture, the cam means having an axis of rotation and wherein the cam means is configured to rotate relative to the hub body and being adapted to secure the suture when in a first rotational position and being adapted to allow movement of the suture when in a second rotational position;
- a rotatable lever handle linked to the cam means for moving the rotatable barrel between the first rotational position and the second rotational position;
- a locking mechanism provided in connection with the rotatable lever handle, the locking mechanism configured to secure the rotational position of the rotatable lever handle, wherein the locking mechanism comprises one or more slots on one of the cam means and the hub body and one or more projections on the other of the cam means and the hub body, the one or more slots cooperatively engaging the one or more projections when the locking mechanism is actuated; and
- a release mechanism comprising a release slot allowing the user to disengage the one or more projections and the one or more slots for allowing movement of the rotatable lever handle subsequent to actuation of the locking mechanism, wherein the user urges the rotatable lever handle in a direction parallel to the axis of rotation of the cam means to actuate the locking mechanism.

6. The drainage catheter hub of claim 5, wherein the cam means comprises a rotatable barrel.

7. The drainage catheter hub of claim 5, wherein the cam means comprises a cam surface.

8. The drainage catheter hub of claim 5, wherein the rotatable lever handle is positioned on a top side of the hub body.

9. The drainage catheter hub of claim 8, wherein the rotatable lever handle is positioned so as to rotate around the outer circumference of the catheter hub.

10. The drainage catheter hub of claim 5, wherein the rotatable lever handle is positioned on a lateral side of the hub body.

11. A drainage catheter for use in providing a fluid pathway for draining bodily fluid from a cavity or tissue of a patient, the drainage catheter being configured such that a suture utilized in connection with the drainage catheter selectively secures the distal end of the catheter in an anchor configuration, the drainage catheter comprising:
- a catheter tube having a proximal end and a distal end, the distal end of the catheter tube being configured to be positioned in tissue, cavity, or other location within the body of the patient having an amount of fluid to be drained;
- a suture running the length of at least a portion of the catheter tube and being secured to the distal end of the catheter tube to selectively maintain the anchor configuration of the distal end of the catheter;
- a catheter hub coupled to the proximal end of the catheter tube, the catheter hub comprising:
  - a seat having an inner contact surface and adapted to be in contact with a portion of the suture;
  - a locking cam adapted to be positioned in the seat, the locking cam having an axis of rotation and an outside diameter, the outside diameter adapted to conform to the inner contact surface of the seat and a tapered camming surface having a release portion and a securement portion, the tapered camming surface extending inwardly from the outside diameter such that the release portion of the tapered camming surface has a greater displacement from the inner contact surface of the seat than the securement portion, wherein the suture can be moved by the user when the locking cam is rotated such that the suture is located between the release portion and the inner contact surface of the seat and when the locking cam is rotated such that the suture is located between the securement portion and the inner contact surface, the suture is cooperatively engaged between the inner contact surface and the securement portion to prevent movement of the suture;

a rotatable lever handle integrally coupled to the locking cam to rotate the locking cam between a position in which the securement portion contacts the suture to prevent movement of the suture and a position in which the release portion contacts the suture to allow movement of the suture;

a locking mechanism provided in connection with the rotatable lever handle, the locking mechanism configured to secure the rotational position of the rotatable lever handle, wherein the locking mechanism comprises one or more slots on one of the locking cam and the hub body and one or more projections on the other of the locking cam and the hub body, the one or more slots cooperatively engaging the one or more projections when the locking mechanism is actuated; and a release mechanism comprising a release slot allowing the user to disengage the one or more projections and the one or more slots for allowing movement of the rotatable lever handle subsequent to actuation of the locking mechanism, wherein the user urges the rotatable lever handle in a direction parallel to the axis of rotation of the locking cam to actuate the locking mechanism.

* * * * *